United States Patent
Floess et al.

(10) Patent No.: US 10,492,781 B2
(45) Date of Patent: Dec. 3, 2019

(54) TENDON FIXATION PLATE

(71) Applicant: PROKON-LP ENGINEERING GMBH, Albstadt (DE)

(72) Inventors: Lukas Floess, Verubgebstadt (DE); Peter Oblak, Albstadt (DE); Stefan Welte, Albstadt (DE)

(73) Assignee: Inovedis GmbH, Albstadt (DE)

( * ) Notice: Subject to any disclaimer, the term of this patent is extended or adjusted under 35 U.S.C. 154(b) by 415 days.

(21) Appl. No.: 15/384,522

(22) Filed: Dec. 20, 2016

(65) Prior Publication Data

US 2017/0181840 A1  Jun. 29, 2017

(30) Foreign Application Priority Data

Dec. 23, 2015 (DE) .................. 10 2015 122 730

(51) Int. Cl.
| | | |
|---|---|---|
| *A61B 17/064* | (2006.01) | |
| *A61F 2/08* | (2006.01) | |
| *A61B 17/80* | (2006.01) | |
| *A61B 17/84* | (2006.01) | |

(52) U.S. Cl.
CPC ........ *A61B 17/0642* (2013.01); *A61B 17/808* (2013.01); *A61B 17/809* (2013.01); *A61B 17/8085* (2013.01); *A61B 17/846* (2013.01); *A61F 2/0811* (2013.01); *A61B 2017/0641* (2013.01); *A61F 2002/0817* (2013.01); *A61F 2002/0829* (2013.01); *A61F 2220/0016* (2013.01)

(58) Field of Classification Search
CPC ... A61B 17/064; A61B 17/0642; A61B 17/80; A61B 17/808; A61B 17/8085; A61B 17/809; A61B 2017/0641

USPC .......................................................... 606/75
See application file for complete search history.

(56) References Cited

U.S. PATENT DOCUMENTS

| | | | |
|---|---|---|---|
| 5,314,427 A | | 5/1994 | Goble et al. |
| 5,449,359 A | * | 9/1995 | Groiso ............... A61B 17/0642 411/459 |
| 5,527,341 A | | 6/1996 | Gogolewski et al. |
| 5,779,707 A | * | 7/1998 | Bertholet ........... A61B 17/8004 606/301 |

(Continued)

FOREIGN PATENT DOCUMENTS

| | | |
|---|---|---|
| DE | 692 06 693 T2 | 5/1996 |
| DE | 603 07 453 T2 | 3/2007 |

(Continued)

OTHER PUBLICATIONS

European Search Report, European Application No. 16204600.7, dated May 22, 2017 (6 pages).

*Primary Examiner* — Eric S Gibson
(74) *Attorney, Agent, or Firm* — Burr & Brown, PLLC

(57) ABSTRACT

An implant for planar connection of tissue to bone is proposed, wherein the implant including a clamping surface and at least three securing members connected to the clamping surface, and wherein the clamping surface comprises an outer edge and an inner edge, wherein the outer edge is connected at least partially to the inner edge at least partially by at least one connecting web, and/or the clamping surface comprises an outer edge and at least one opening arranged within the clamping surface, which opening is connected by at least one connecting web at least to a partial area of the outer edge of the clamping surface.

15 Claims, 5 Drawing Sheets

(56) References Cited

U.S. PATENT DOCUMENTS

| | | | |
|---|---|---|---|
| 6,712,822 B2* | 3/2004 | Re | A61B 17/0642 606/219 |
| 7,572,276 B2 | 8/2009 | Lim et al. | |
| 2007/0191850 A1* | 8/2007 | Kim | A61B 17/0642 606/75 |
| 2008/0319443 A1* | 12/2008 | Focht | A61B 17/0642 606/75 |
| 2010/0094358 A1* | 4/2010 | Moore | A61B 17/0642 606/319 |
| 2010/0125275 A1* | 5/2010 | Kinmon | A61B 17/0642 606/75 |
| 2010/0145386 A1 | 6/2010 | Greenhalgh et al. | |
| 2012/0130374 A1* | 5/2012 | Bouduban | A61B 17/0642 606/75 |
| 2012/0228355 A1 | 9/2012 | Combrowski et al. | |
| 2013/0338720 A1* | 12/2013 | Kleiner | A61B 17/025 606/304 |
| 2015/0230839 A1* | 8/2015 | Riccione | A61B 17/8014 606/297 |

FOREIGN PATENT DOCUMENTS

| | | |
|---|---|---|
| DE | 10 2007 045 886 A1 | 4/2009 |
| DE | 10 2012 100 086 A1 | 8/2012 |
| EP | 0 852 128 B1 | 7/2001 |
| EP | 2 581 046 A1 | 4/2013 |
| FR | 2 980 966 A1 | 4/2013 |
| WO | 00/64365 A1 | 11/2000 |

* cited by examiner

TENDON FIXATION PLATE

This application claims the benefit under 35 USC § 119(a)-(d) of German Application No. 10 2015 122 730.4 filed Dec. 23, 2015, the entirety of which is incorporated herein by reference.

FIELD OF THE INVENTION

The present invention relates to an implant for planar connection of tissue to bone, and a system for connecting tissue to bone, comprising at least one implant and at least one tool.

BACKGROUND OF THE INVENTION

Various circumstances can lead to a surgical intervention having to be performed in order to fix and reconstruct torn tissues, e.g. tendinous tissue. In this regard, it is known from the prior art that, in order to reconstruct a tendon for example, the torn-off end of the latter is fixed to the bone by means of an implant. The terms anchor and bone anchor are also commonly used by a person skilled in the art for such an implant. For example, an anchor of this kind is disclosed in EP 2 581 046 A1. Such an anchor is usually driven into the bone for securing purposes. This generally necessitates corresponding preliminary treatment of the bone, for example, to provide a suitable drilled hole for the anchor. By means of a suture thread, which is connected or connectable to the anchor, the tissue, for example the tendon, is fixed in such a way that the end of the tissue has suture thread looped around it and is thus fixed for incorporation on the bone. A disadvantage of this is, in particular, that the fixation of the tendon takes more time and therefore entails increased costs.

It is also a disadvantage that the fixation of the tendon may not have sufficient stability, for example, on account of incorrect procedure during the fixation. The prior art in EP 0 852 128 B1 discloses a surgical clip for connecting two bone parts or for connecting tendons or ligaments to bone parts, which clip has two securing members. Here, one securing member is arranged, for example, in the area of a bone part and one securing member is arranged, for example, in the area of a tendon or of a ligament. It is a disadvantage here that such a connection in some cases has insufficient stability or that detachment of the tissue from the bone takes place, such that a further surgical intervention is required in the event of such detachment.

SUMMARY OF THE INVENTION

The object of the present invention is, therefore, to make available a possibility for securing tissue to bone in the context of a surgical intervention which, while minimizing necrotic processes, can be performed with less expenditure in terms of work and time.

To achieve the object, an implant for planar connection of tissue to bone is proposed. According to the present invention, provision is made that the implant comprises a clamping surface and at least three securing members connected to the clamping surface. It is thus possible to connect tissue to bone without using suture threads. The connection of tissue and bone takes place, in particular, via the clamping surface. This permits a planar connection of tissue to bone and pressing of the tissue onto the bone. The time required to do this in a surgical intervention can thus be significantly reduced. At least three securing members ensure a sufficient hold of the implant. Advantageously, therefore, a duration of treatment after a surgical intervention can also be reduced, since follow-up treatment is made considerably easier. In this way, treatment costs can also be reduced. According to the present invention, provision is made that the clamping surface comprises an outer edge and an inner edge, wherein the outer edge is connected at least partially to the inner edge at least partially by means of at least one connecting web, and/or the clamping surface comprises an outer edge and at least one opening arranged within the clamping surface, which opening is connected by means of at least one connecting web at least to a partial area of the outer edge of the clamping surface.

After the implant has been introduced, a clamping surface which comprises an outer edge, an inner edge and connecting webs or openings can advantageously suppress the advance of necrotic processes in the case of a planar connection of tissue and bone. No treatment is, therefore, needed after implantation of the implant or after connection of tissue and bone.

It is also advantageous that punctiform pressure peaks are avoided, as a result of which a sufficient flow of blood can be ensured. Moreover, the implant is able to exert a continuous contact pressure, which can be maintained over the entire period of incorporation. To this extent, more rapid incorporation can be permitted.

In a development, provision can be made that at least one securing member is formed integrally on the clamping surface, and/or at least one securing member is cone-shaped, and/or the at least one securing member comprises at least one barb.

Securing members formed integrally on the clamping surface are able to increase the stability or the hold of the fitted implant. Barbs on the securing member can promote a firm hold of the implant. If a securing member is cone-shaped, this can speed up the introduction of the implant during a surgical intervention.

In a development, provision can be made that at least two securing members are arranged approximately parallel to each other and/or have different lengths, and/or that the clamping surface forms a plane, wherein at least one securing member is arranged approximately perpendicular to the plane and/or at least one securing member is arranged approximately parallel to the plane. By virtue of the different configuration or arrangement of the securing member, it is possible for different anatomical circumstances to be taken into account. This can result in less time being spent in a surgical intervention. This can furthermore result in an improved hold of the implant and, consequently, a firm connection between tissue and bone.

In an advantageous development, provision can be made that the clamping surface comprises a tool engagement surface. In this way, a tool can be fitted directly on the implant in order to introduce the implant or to connect tissues and bone to each other. In this way, the time required to connect bone and tissue can be significantly reduced.

Provision can moreover be made that the clamping surface comprises at least one projection, which has at least one opening. In this way, a further possibility for securing the implant is made available. The introduction of the implant in a surgical intervention can also be simplified. For example, a further securing member can be used which is arranged in the opening of the projection and connects tissue and bone to each other.

It can also be permitted that the implant can be secured to tissue and additionally to the bone.

According to the present invention, provision can be made that the projection has a length of between 5 mm and 20 mm, preferably of between 6 and 13 mm. It is particularly advantageous if the projection has a length of 6.5 mm or 12.5 mm.

In a development, provision can be made that the clamping surface comprises at least one projection, wherein the at least one projection is arranged along a transverse extent of the clamping surface, and/or the at least one projection and the clamping surface are formed in one piece. This represents a further possibility for securing the implant, for example, to the bone. In this way, after introduction of the implant, it is possible for the connection between tissue and bone to withstand increased loads. Therefore, it is possible to avoid treatments following connection of tissue and bone by means of the implant.

In a preferred embodiment, provision can be made that the clamping surface comprises at least two oblong holes which each taper conically and are arranged diametrically. It is thus possible that a tool can be introduced and/or withdrawn by means of a rotation movement. Such interaction of tool and implant, which can represent a system, can be understood as a bayonet lock. It is thereby possible to simplify and speed up the introduction of the implant in a surgical intervention. Moreover, after introduction of the implant, the oblong holes in the clamping surface can reduce necrotic processes, since the oblong holes can be regarded as a cutout or opening in the clamping surface.

Within the meaning of the invention, the term cutout can be regarded as synonymous with the term opening.

In a development, provision can be made that the clamping surface has an at least partially rounded circumference and/or is at least partially curved. It is thus possible to take individual anatomical circumstances into account. In this way, it is possible to simplify and speed up the introduction of the implant or the connection of tissue and bone. Moreover, a stable hold of tissue and bone can be achieved. Moreover, a more uniform pressing of the tissue on the entire surface area of the clamping surfaces is thereby achieved. A clamping surface with a curved shape has the advantage of permitting simple modeling of the implant to the bone.

In a particularly advantageous manner, provision can be made that the clamping surface has a substantially oval circumference. In this way, it is possible to provide the largest possible contact surface or clamping surface of the implant.

Provision can be made that the clamping surface has a longitudinal extent in a range of between 2 mm and 30 mm, preferably between 5 mm and 20 mm, and/or that the clamping surface has, at least in a predominant partial area, a thickness of between 0.2 mm and 4 mm, preferably of between 0.3 mm and 3 mm, and/or that at least the clamping surface is made of a metallic material, in particular titanium, or of a plastic, in particular a biocompatible plastic. A clamping surface made of a metallic material, in particular titanium, or of a plastic, in particular a biocompatible plastic, has, on the one hand, sufficient stability for connecting tissue and bone to each other. On the other hand, such materials are very compatible with the human body. Longitudinal extents of the clamping surface in a range of between 2 mm and 30 mm, preferably of between 5 mm and 20 mm, are particularly advantageous for the connection of tendon and bone, particularly in the area of the human shoulder. This applies equally to thicknesses of between 0.2 mm and 4 mm, preferably of between 0.3 mm and 3 mm. It is particularly advantageous if the clamping surface of the implant is 20 times 15 mm or 14 times 10 mm. The numbers relate here to length times width or longitudinal extent and transverse extent. Such clamping surfaces can permit a particularly secure and stable fixation of tissue to bone.

Provision can be made that the clamping surface comprises at least one fixing member, which is preferably arranged on an underside. This permits fixation of the clamping surface to the tissue. This can simplify the securing of tissue to bone and strengthen the connection of tissue and bone.

According to the present invention, the fixing members can also be designated as spikes. These can prevent slipping of the tissue, for example, of a tendon.

In a development of the invention, provision can be made that the implant comprises a clamping surface which has a substantially rectangular shape and on which at least four integrally formed securing members are arranged.

Provision can also be made that a projection comprises at least one fixing member. In this way, the connection of tissue and bone can be further strengthened. According to the present invention, provision can be made that a ratio of the sum of the surface areas of the openings of the clamping surface and of the oblong holes to the total surface area of the clamping surfaces is 30% to 70%, in particular 40% to 60%.

According to the present invention, provision can also be made that approximately 50% of the total surface area of the clamping surface has openings. This can include oblong holes.

It is thus possible to obtain an optimized ratio between openings and total surface area, i.e. an optimized ratio between contact surface and thus securing of the implant and openings or to permit flow of blood through the tissue and thus minimize necrotic processes.

The present invention can also provide an implant in which the clamping surface has a substantially rectangular circumference and which comprises four securing members integrally formed at respective corners of the clamping surface. Such an implant can permit particularly stable securing of tissue and bone. Such an implant can be used, for example, but not exclusively, in the field of veterinary medicine.

The present invention can moreover provide an implant that has a substantially round shape, in particular an oval shape, wherein the implant comprises four securing members arranged integrally on the clamping surface.

Here, provision can preferably be made that the clamping surface has lengths of 6 mm to 24 mm and widths of 4 mm to 22 mm. In particular, provision is made that the clamping surface has a length of 6 mm and a width of 8 mm, or a length of 10 mm and a width of 8 mm, or a length of 12 mm and a width of 10 mm, or a length of 14 mm and a width of 12 mm, or a length of 16 mm and a width of 14 mm, or a length of 18 mm and a width of 16 mm.

The present invention also relates to a system for connecting tissue to bone, comprising at least one implant and at least one tool, wherein the tool comprises a gripping member and a shaft arranged thereon for conjoint rotation, wherein the tool comprises a driving profile, wherein the driving profile comprises a base and at least two holding members, wherein the implant comprises a clamping surface and at least three securing members connected to the clamping surface.

According to the present invention, provision can moreover be made that, in the system, the implant is configured according to the disclosed features.

According to the present invention, provision can be made that the driving profile comprises a base and at least two holding members. This permits a hold of the tool on an implant and, moreover, a positioning of the tool. In this way, the tool can be used to allow an implant for connecting tissue to bone to be inserted in a manner that is particularly efficient in terms of the time taken.

In a development, provision can be made that the at least two holding members are connected to the base, and/or the driving profile comprises a base which has a greater circumference than a circumference of the shaft and/or is integrally connected to the shaft. Holding members connected to the base can increase the stability of the tool. This permits secure and complete introduction of the implant. This applies equally in the case where the base has a greater circumference than a circumference of the shaft. This can result in an improved distribution of force to the implant during the introduction of the implant.

Provision can be made that the base and the shaft are formed in one piece and/or the at least two holding members are preferably configured as lugs and have a substantially round or polygonal circumference. A tool of this kind can be produced cost-effectively and is robust, as a result of which a smooth and efficient introduction of the implant can also be permitted.

The present invention can also provide that the base and the shaft can be connected releasably. This permits the provision of a more versatile tool with a shaft. It is thus possible to connect different base configurations to one tool.

A releasable connection of this kind between base and shaft can be obtained using a securing member. The securing member can be designed as a nut, for example.

It is possible that the at least two holding member have a substantially round circumference and/or each have a preferably circumferential groove. The tool can thus engage in and be held in the implant. This permits simple introduction of the implant.

In an advantageous development, provision can be made that the base comprises at least one positioning member. This can provide a possibility of orientation when placing the tool onto the implant. It is thus possible to counteract an incorrect introduction of the implant.

It is also possible that the base has a surface that is recessed in such a way that a workpiece, in particular an implant, can be guided and/or held with form-fit engagement within the surface. This can simplify and speed up the introduction of the implant.

In the system according to the present invention, the connection of tissue and bone is effected, in particular, via the clamping surface of the implant. This permits a planar connection of tissue to bone or a pressing of the tissue onto the bone. In combination with a tool in which a driving profile comprises a base and at least two holding members, this allows the tool to be held on an implant and additionally permits a positioning of the tool or of the implant. In this way, the tool can be used to allow an implant for connecting tissue to bone to be inserted in a manner that is particularly efficient in terms of the time taken. The time required for a surgical intervention or for introduction of the implant can thus be significantly reduced, since it is not necessary to apply suture material. Securing members on the implant permit a sufficient hold of the implant.

Provision can also be made that the implant comprises at least one projection, which comprises at least one opening into which at least one nail can be inserted in such a way that the implant can be secured on the bone. An additional securing member permits more stable securing of the implant to the bone.

Within the meaning of the present invention, the nail can also be designated and understood as an anchor. Securing members of this kind can be produced cost-effectively and permit a stable connection between bone and implant.

According to the present invention, provision can thus also be made that the system comprises an implant, a tool and a nail. To this extent, provision can be made that the system is in at least three parts.

BRIEF DESCRIPTION OF THE DRAWINGS

An illustrative embodiment of the present invention is explained in more detail below with reference to drawings in which.

DETAILED DESCRIPTION OF THE INVENTION

Figure 1:
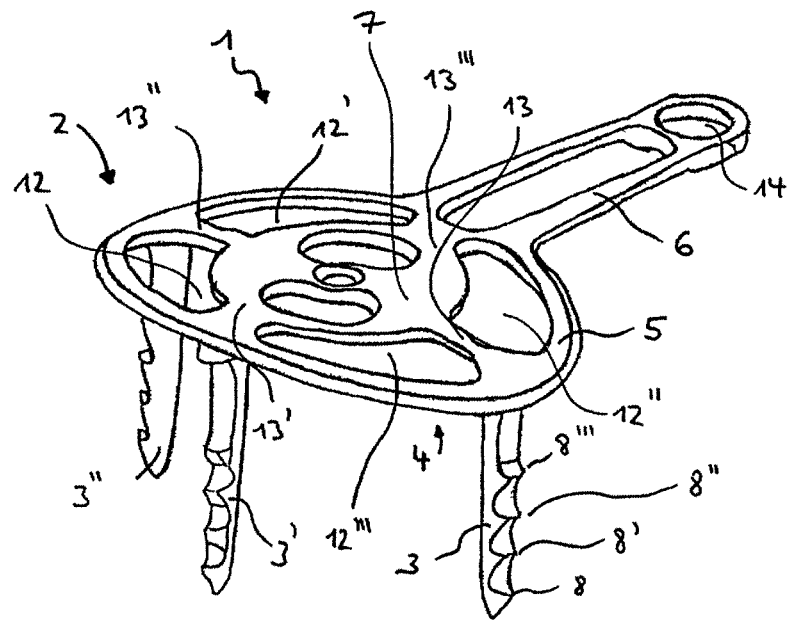
FIG. 1 shows an implant according to the invention in a perspective view.

FIG. 1 shows a perspective view of an implant 1 according to the present invention. With the clamping surface 2 of the implant 1, tissue, e.g. tendinous tissue, is secured on a bone (see FIG. 7 and FIG. 8). The clamping surface 2 has an at least partially round circumference. Moreover, the clamping surface 2 is at least partially curved. The clamping surface 2 forms a plane.

The implant 1 comprises a clamping surface 2 and three securing members 3, 3', 3", which are each formed integrally on the clamping surface 2. The view shows that the securing member 3, 3', 3" are integrally formed on an underside 4 of the clamping surface 2. The securing member 3, 3', 3" thus have a conical shape at their side directed away from the clamping surface 2. In this way, the securing member 3, 3', 3" can be introduced particularly effectively into a tissue or into a bone. The view moreover shows that the securing members 3, 3', 3" comprise barbs 8, 8', 8" and 8'''. These are provided in order to prevent detachment of the implant 1 after the connection of tissue and bone.

The clamping surface 2 comprises an outer edge 5 and an inner edge 7, wherein the outer edge 5 is connected at least partially to the inner edge 7 at least partially by means of connecting webs 13, 13', 13", 13'''.

Moreover, the implant 1 comprises openings 12 to 12'''' arranged within the clamping surface 2. The openings 12, 12', 12", 12''', 12'''' are connected by means of connecting webs 13, 13', 13", 13''' at least to a partial area of the outer edge 5 of the clamping surface 2. In a planar connection of implant 1 to tissue or bone, the openings 12, 12", 12''', 12'''' allow blood to flow through the tissue. This therefore counteracts necrotic processes.

The clamping surface 2 moreover comprises a projection 6, which has an opening 14. A nail (see FIG. 7) or similar holding member can be guided through this opening 14 in order to connect the implant 1 in the area of this opening 14 to a bone or to tissue. The implant 1 can thereby be connected to tissue or bone in a particularly stable manner and thus permits a stable connection between tissue and bone. The projection 6 is arranged approximately along a transverse extent 23 of the clamping surface 2. Moreover, the projection 6 and the clamping surface 2 are formed in one piece. The longitudinal extent 22 of the clamping surface 2 is also shown.

Figure 2:
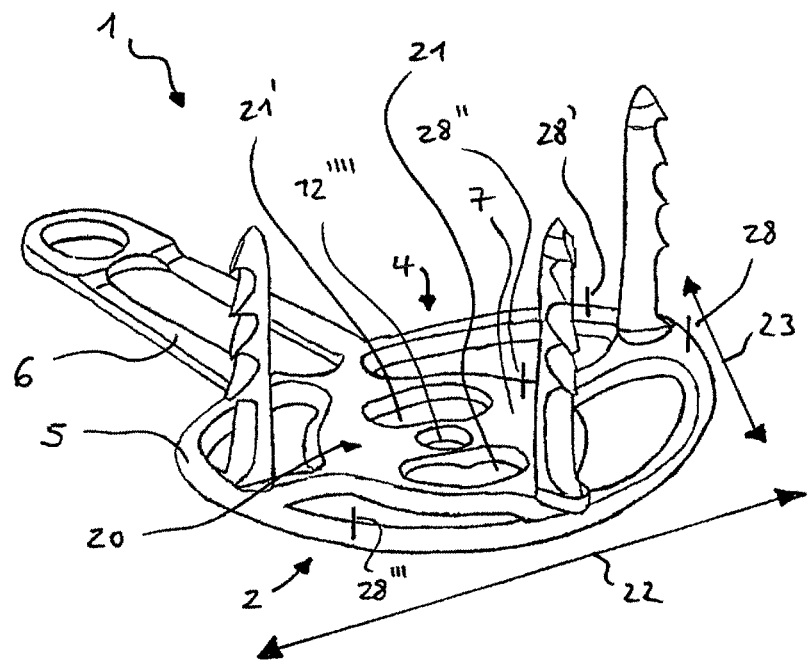
FIG. 2 shows an implant according to the invention in a further perspective view.

FIG. 2 shows a further perspective view of the implant 1 from FIG. 1, revealing that the clamping surface 2 comprises a further opening 12'''' more or less at its center.

It is also seen that the clamping surface 2 comprises a tool engagement surface 20. In this way, the implant can be implanted particularly easily and in less time.

The tool engagement surface can be configured in the form of oblong holes 21, 21'. The oblong holes can be regarded as analogous to the openings 12 to 12'''' (see FIG. 1) and suppress necrotic processes. In the illustrative embodiment, the oblong holes 21, 21' are each designed as conically tapering oblong holes 21, 21', which are arranged diametrically in such a way that a tool (see FIG. 3) can be introduced and/or withdrawn at least by means of a rotation movement. It is of particular importance here that a tool can be withdrawn by means of a rotation movement in such a way that the implant 1 does not change its position, i.e. is not unscrewed by, for example, a rotation movement of the tool.

The oblong holes 21, 21' have a substantially kidney-shaped configuration. The oblong holes 21, 21' can interact in the manner of a bayonet with a tool (not shown).

It will also be seen that the clamping surface 2 comprises fixing members 28, 28', 28'', 28''' and 28''''. The clamping surface 2 thus comprises at least one fixing member 28. The at least one fixing member 28 is preferably arranged on the underside 4 of the clamping surface 2 and has a preferably cylindrical configuration. The at least one fixing member 28 can, in particular, fix the tissue and thereby facilitate the connection or securing of tissue and bone or strengthen the connection of tissue and bone. Moreover, the at least one fixing member 28 can permit an improved hold of the clamping surface 2 on tissue.

Provision can be made that the at least one fixing member 28 is arranged on an outer edge 5 and/or on an inner edge 7 of the clamping surface 2. In this way, the connection of clamping surface 2 and tissue can be strengthened in a specific manner.

Provision can moreover be made that the at least one fixing member is preferably integrally formed in one piece on the clamping surface 2. The stability of the fixing member 28 can thereby be increased.

Figure 3:
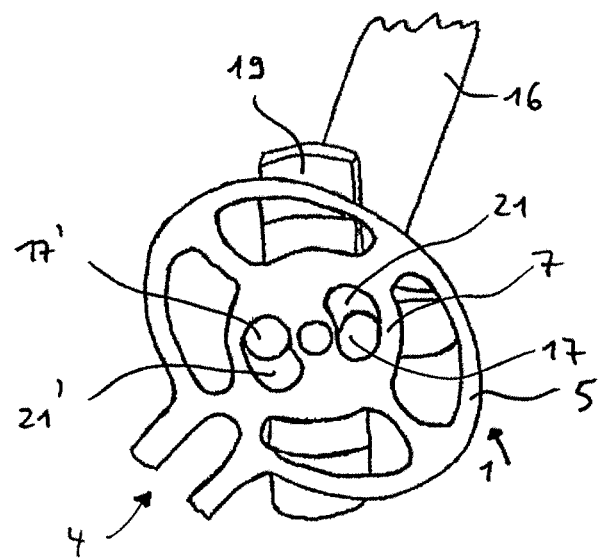
FIG. 3 shows a system (tool and implant) according to the invention in a perspective view.
Figure 5:
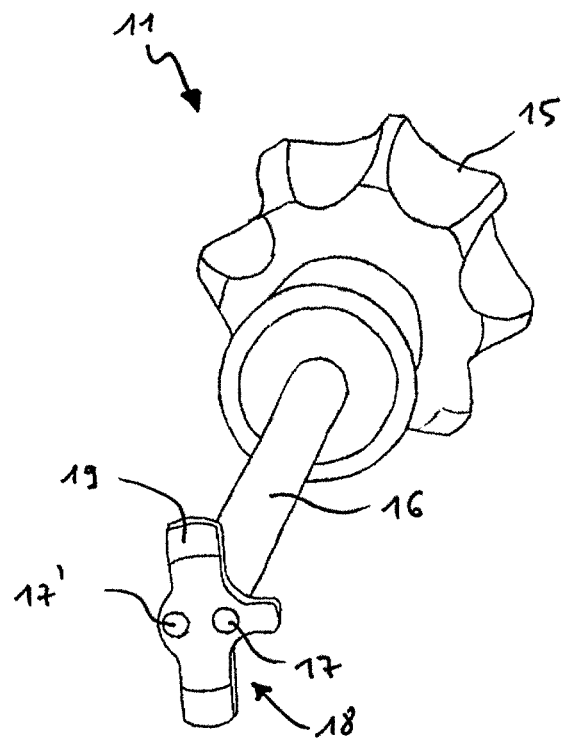
FIG. 5 shows a schematic view of the tool from FIG. 3.

FIG. 3 shows a system according to the present invention for connecting tissue (not shown) to bone (not shown), the system comprising an implant 1 and a tool 11. A detail of an arrangement of the implant 1 from FIG. 1 in combination with the tool 11 according to FIG. 5 is shown. The implant 1 shown from the underside 4 in FIG. 3.

It will be seen from FIG. 3 that two holding members 17, 17', which are arranged on the base 19 of the tool connected to the shaft 16, interact with conically tapering oblong holes 21, 21' on the implant 1 or on the clamping surface 2 thereof. The conical tapers of the oblong holes 21, 21' are arranged diametrically in such a way that the holding members 17, 17' or the tool 11 can be inserted and/or withdrawn by means of a rotation movement. A tool 11 can therefore interact with the clamping surface 2 of the implant 1 in the manner of a bayonet. The clamping surface 2 therefore has a tool engagement surface 20 (see also FIG. 4).

Figure 4:
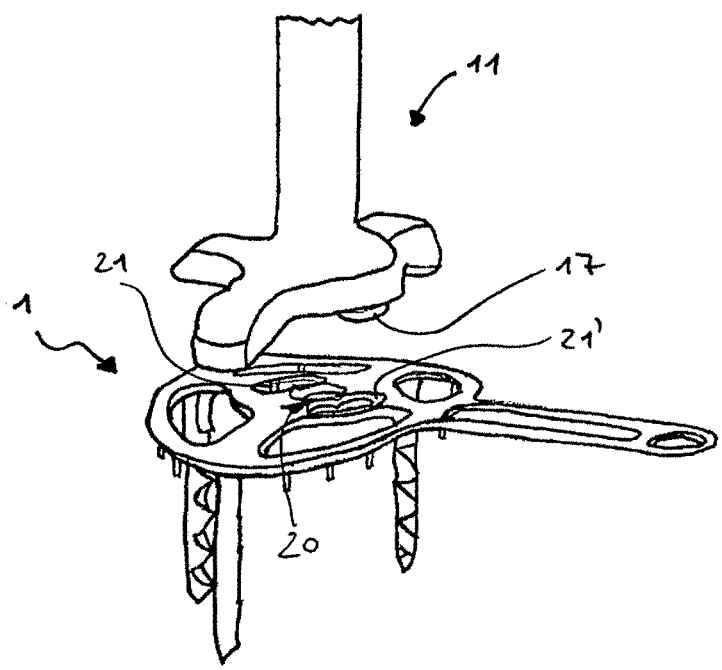
FIG. 4 shows a further schematic view of the system (tool and implant)

FIG. 4 shows a further schematic view of the system, comprising a tool 11 and an implant 1. The holding member 17 of the tool 11 can interact with the tool engagement surface 20 of the implant 1 and thus permit introduction of the implant 1, for example into a human body, in a particularly simple manner.

A bayonet-like interaction of tool engagement surface 20 (by means of oblong holes 21, 21') and tool 11 (by holding members 17, 17') also ensures that, after the implant 1 has been introduced into a human body, the tool 11 can thereafter be separated or removed particularly easily from the implant 1.

It is of particular advantage that, upon removal of the tool 11, the position of the implant 1 is not impaired, or a stable securing of tissue to bone by the implant 1 is not impaired.

FIG. 5 shows a tool 11 in a perspective view. The tool 11 is provided for the placement of the implant 1 for connecting tissue to bone. The tool 11 comprises a gripping member 15, and a shaft 16 arranged thereon for conjoint rotation. The tool 11 moreover comprises a driving profile 18.

The driving profile 18 here comprises a base 19 and two holding members 17, 17', which are able to interact with a tool engagement surface on the implant and can thus permit easier implantation of the implant. The holding members 17, 17' are designed as lugs and have a substantially round circumference.

The holding members 17, 17' are connected to the base 19, which has a greater circumference than a circumference of the shaft 16. Moreover, the base 19 is connected in one piece to the shaft 16. Furthermore, the base 19 and the shaft 16 are formed in one piece.

Figure 6:
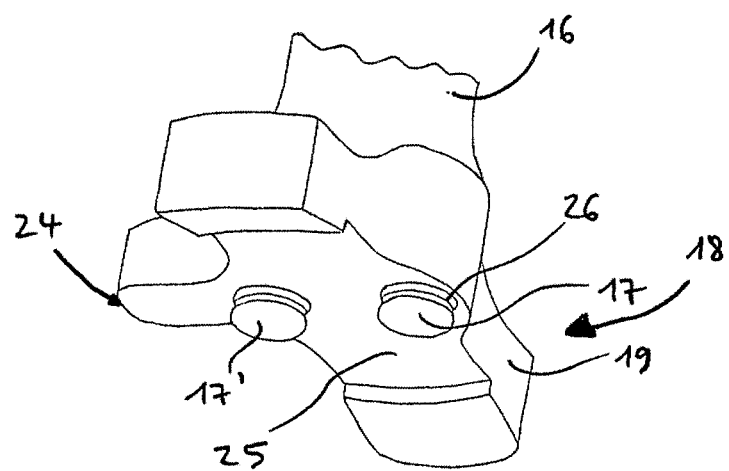
FIG. 6 shows a schematic view of a detail of the tool from FIG. 3.

FIG. 6 shows an enlarged detail of the tool from FIG. 5, this detail showing that the base 19 has a surface 25 recessed in such a way that a workpiece, in particular the implant (not shown), can be guided and/or held with form-fit engagement within the surface 25.

Arranged within the surface 25 are the holding members 17, 17', which each have a preferably circumferential groove 26, 26'. The base 19 moreover comprises a positioning member 24.

According to the present invention, provision is made that the surface 25 of the tool 11 interacts with form-fit engagement with the clamping surface of the implant (not shown). In this way, the clamping surface or the implant is held by the tool 11 during introduction of the implant, for example, into a human body. The introduction of the implant can thus be made significantly easier.

Figure 7:
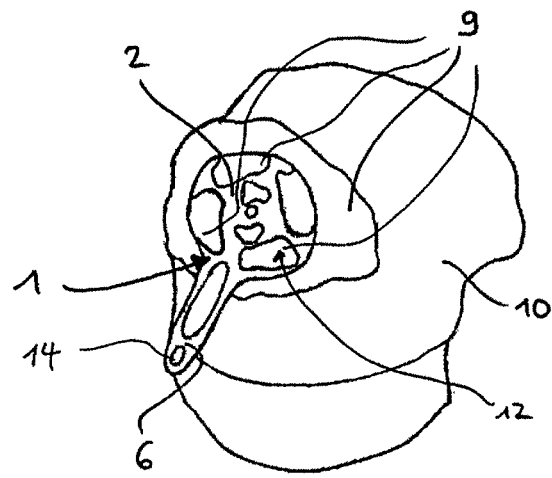
FIG. 7 shows a schematic view of the implant for connecting tissue and bone.

FIG. 7 shows a schematic view of the implant 1 for connecting tissue 9 and bone 10. The tissue 9, in particular tendinous tissue, is here pressed onto a bone by means of the implant 1. For this purpose, the implant 1 comprises a clamping surface 2. The clamping surface 2 thus permits securing or connecting of the tissue 9 to bone 10 without using a suture thread or the like. To avoid accidental detachment of the implant 1, the latter comprises securing members (not shown), which are arranged on the clamping surface 2 (see FIG. 1).

When the implant 1 is applied and pressed onto tissue 9, tissue 9 is pressed through openings 12. In some cases, the tissue 9 may also protrude bulge-like through the openings 12. Tissue is not covered by the openings 12, and the oblong holes 21, 21a (see FIG. 1 for example) of the clamping surface 2 of the implant 1. In this way, the tissue 9 can be afforded a sufficient circulation of blood and does not die, i.e. necrotic processes are suppressed or minimized.

To this extent, the tissue 9 is not covered completely by the clamping surface 2 of the implant 1. At the same time, however, the planar pressing-on of the implant 1 or of the clamping surface 2 permits fixing of the tissue 9 and a stable connection of the tissue 9 to bone 10. This is also permitted by an inner edge and an outer edge of the clamping surface 2 (FIG. 1).

Figure 8:
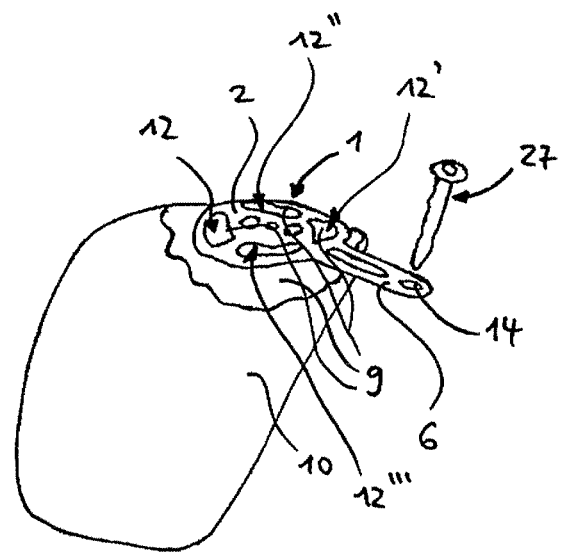
FIG. 8 shows a further schematic view of the implant for connecting tissue and bone.

FIG. 8 shows schematically that the securing of the implant 1 on a bone 10 can be done using a nail 27. The nail 27 can be arranged in an opening 14 in the projection 6 of the implant 1. It is also possible that, after introduction of the nail 27, the projection 6 is bent in order to be connected to the bone 10. For this purpose, provision can be made that the projection 6, at a transition area to the clamping surface 2, has a smaller material thickness than the clamping surface 2. The projection 6 can thus be bent particularly easily in this area, which can be designated as a weakening. It is thus possible to take individual anatomical circumstances into account.

The nail 27 can be understood as a further securing member which is not connected in one piece to the clamping surface 2. By using a nail 27, the implant 1 can be additionally secured, for example, on a bone 10. This also has an advantageous effect as regards connecting tissue 9 and bone 10. The implant 1 can thus be understood as a tendon fixation plate.

Figure 9:
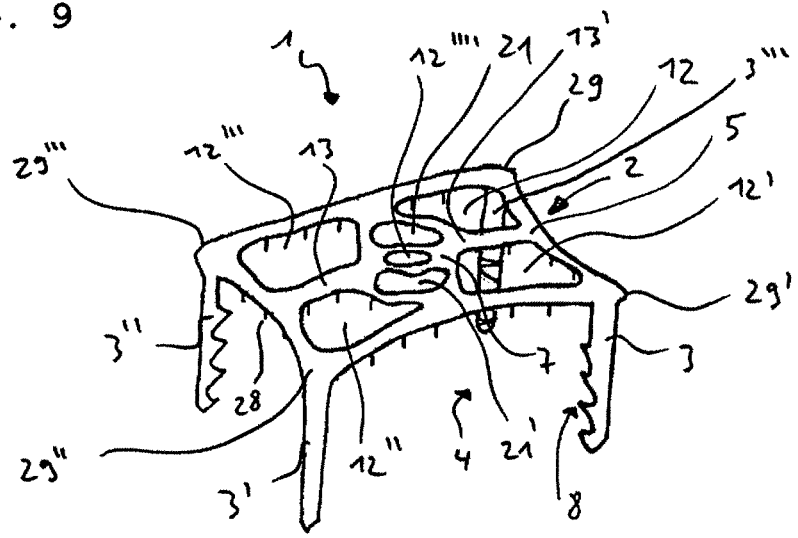
FIG. 9 shows a schematic view of a further embodiment of the implant according to the invention.
Figure 10:
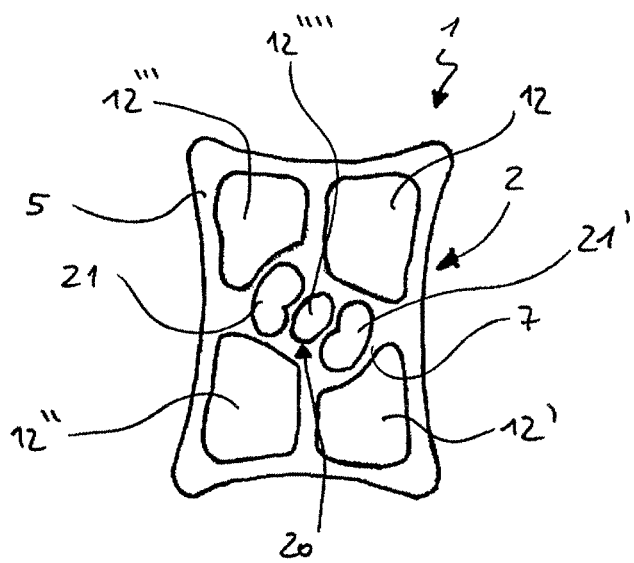
FIG. 10 shows a further view, namely a plan view, of the implant from FIG. 9.

FIGS. 9 and 10 show a further embodiment of the implant 1. The implant 1 comprises a clamping surface 2. In contrast to the implant shown in FIG. 1, the implant 1 shown in FIG. 9 comprises a clamping surface 2 with a substantially rectangular circumference. In the illustrative embodiment shown, the clamping surface comprises four securing members 3, 3', 3", 3''' formed integrally at respective corners 29, 29', 29", 29''' of the clamping surface 2.

The clamping surface 2 comprises an outer edge 5 and an inner edge 7, wherein the outer edge 5 is at least partially connected to the inner edge 7 at least partially by means of connecting webs 13, 13'.

In the illustrative embodiment shown, the implant 1 is depicted without a projection. However, within the scope of the invention, provision can be made that at least one projection is formed preferably integrally on the clamping surface 2.

The implant 1 comprises a tool engagement surface 20, which is preferably formed by two diametrically arranged oblong holes 21, 21', which taper conically.

The clamping surface 2 comprises a centrally arranged opening 12''' arranged between the oblong holes 21, 21'. Moreover, the clamping surface 2 comprises four further symmetrically arranged openings 12, 12', 12" and 12''''. The openings 12, 12', 12", 12''', 12'''' are connected by means of connecting webs 13, 13' at least to a partial area of the outer edge 5 of the clamping surface 2. Upon planar connection of implant 1 to tissue or bone, the openings 12, 12', 12", 12''', 12'''' allow blood to flow through the tissue. Necrotic processes are thus counteracted.

The oblong holes 21, 21' also by analogy constitute openings and are able to suppress necrotic processes.

Irrespective of the geometric configuration of the implant 1, a ratio of the sums of the openings and optionally of the oblong holes of the clamping surface to the total surface area of the clamping surface can be specified. The openings of the clamping surface and optionally the oblong holes can together be designated as so-called cutouts. The total surface area of the clamping surface is defined by its respective circumference. Any projections are explicitly excluded from this.

It is advantageous if the ratio of the cutouts or of the sum of the surface areas of the opening of the clamping surface and of the oblong holes to the total surface area of the clamping surface is 30% to 70%. It is particularly advantageous if the ratio of the cutouts or of the sum of the surface areas of the openings of the clamping surface and of the oblong holes to the total surface area of the clamping surface is 40% to 60%.

According to the present invention, provision can also be made that about 50% of the total surface area of the clamping surface has openings. This can include oblong holes.

It is thus possible to obtain an optimized ratio between openings and total surface area, i.e. an optimized ratio between contact surface and thus securing of the implant and openings or to permit circulation of blood through the tissue and thus minimize necrotic processes.

FIG. 10 shows the symmetrical arrangement of all the openings 12, 12', 12", 12''' and the symmetrical arrangement of the opening 12'''' centered in the clamping surface 2. Moreover, the symmetrical arrangement of the oblong holes 21, 21' with respect to the opening 12'''' is shown.

Figure 11:
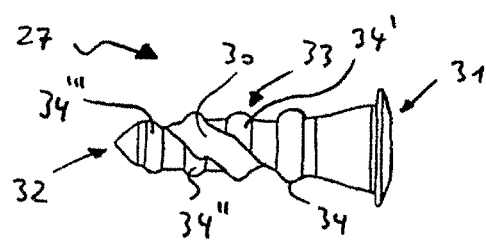
FIG. 11 shows a schematic view of an embodiment of the nail.

FIG. 11 shows a schematic view of an embodiment of the nail 27. The nail 27 comprises a nail shank 33. The nail 27 has a headpiece 31 at one end and a taper 32 at another end. The taper 32 has a conical configuration. In this way, the nail 27 can be more easily driven into a bone. The headpiece 31 can interact with form-fit engagement with the tool (not shown). To make it even easier to drive in the nail 27, the latter has, in the area of the nail shank 33, a preferably circumferential spiral groove 30 (approximately 1 turn/360° along a length of nail 27 of 10 mm). In the illustrative embodiment, the nail 27 has a total length of approximately 13 to 14 mm. In the illustrative embodiment, the nail shank 33 has a total length of approximately 10 mm. In the illustrative embodiment, the nail 27 has a conical configuration and, in the area of the taper 32, has a thickness of approximately 1.5 mm. The thickness in the area of the headpiece 31 is approximately 2.0 to 2.1 mm.

The nail shank 33 moreover comprises a plurality of annular beads 34, 34', 34" and 34'''. In combination with the configuration of the spiral groove 30, these allow the nail 27 to be driven in more easily and provide a secure hold, for example in a bone.

According to the present invention, the nail 27 can be a constituent part of a system comprising a tool and an implant (see FIG. 4).

LIST OF REFERENCE SIGNS 1 implant
2 clamping surface
3 securing member
3' securing member
3" securing member
3''' securing member
4 underside (of clamping surface)
5 outer edge
6 projection
7 inner edge
8 barb
8'-8''' barb
9 tissue
10 bone 11 tool
12 opening (of clamping surface)
12'-12'''' opening (of clamping surface)
13 connecting web
13'-13''' connecting web
14 opening (of projection)
15 gripping member
16 shaft
17, 17' holding member
18 driving profile
19 base
20 tool engagement surface
21 oblong hole
22 longitudinal extent (of clamping surface)
23 transverse extent (of clamping surface)
24 positioning member
25 surface
26, 26' groove
27 nail
28 fixing member
28'-28'''' fixing member
29'-29''' corner (of clamping surface)
30 spiral groove
31 headpiece
32 taper
33 nail shank
34-34''' annular bead

The invention claimed is:

1. An implant for planar connection of tissue to bone, comprising: a clamping surface and at least three securing members connected to the clamping surface, wherein the clamping surface comprises an outer edge and an inner edge, wherein the outer edge is connected at least partially to the inner edge at least partially by at least one connecting web, and/or the clamping surface comprises an outer edge and at least one opening arranged within the clamping surface, which opening is connected by at least one connecting web at least to a partial area of the outer edge of the clamping surface, wherein the clamping surface has at least one projection having at least two openings and at least one fixing member that is arranged on an underside of the clamping surface.

2. The implant according to claim 1, wherein at least one securing member is formed integrally on the clamping surface, and/or at least one securing member is cone-shaped, and/or the at least one securing member comprises at least one barb.

3. The implant according to claim 1, wherein at least two securing members are arranged approximately parallel to each other and/or have different lengths, and/or in that the clamping surface forms a plane, wherein at least one securing member is arranged approximately perpendicular to the plane and/or at least one securing member is arranged approximately parallel to the plane.

4. The implant according to claim 1, wherein the clamping surface comprises a tool engagement surface.

5. The implant according to claim 1, wherein the at least one projection is arranged approximately along a transverse extent of the clamping surface, and/or the at least one projection and the clamping surface are formed in one piece.

6. The implant according to claim 1, wherein the clamping surface comprises at least two oblong holes which each taper conically and are arranged diametrically.

7. The implant according to claim 1, wherein the clamping surface has an at least partially rounded circumference and/or is at least partially curved.

8. The implant according to claim 1, wherein the clamping surface has a substantially rectangular circumference and comprises four securing members formed integrally at respective corners of the clamping surface.

9. The implant according to claim 1, wherein the at least one projection having at least two openings, comprises at least one opening into which at least one nail can be inserted in such a way that the implant can be secured on the bone.

10. The implant according to claim 1, wherein at least one fixing member is arranged on both the underside of the clamping surface and an underside of the at least one projection.

11. A system for connecting tissue to bone, comprising: at least one implant and at least one tool, wherein the tool comprising a gripping member and a shaft arranged thereon for conjoint rotation, wherein the tool comprises a driving profile, wherein the driving profile comprises a base and at least two holding members, wherein the implant comprises a clamping surface and at least three securing members connecting to the clamping surface, wherein the clamping surface comprises an outer edge and an inner edge, with the outer edge connected at least partially to the inner edge at least partially by at least one connecting web, and/or the clamping surface comprises an outer edge and at least one opening arranged within the clamping surface, which opening is connected by at least one connecting web at least to a partial area of the outer edge of the clamping surface, wherein the clamping surface has at least one projection having at least two openings and at least one fixing member that is arranged on an underside of the clamping surface.

12. The system according to claim 11, wherein the at least two holding members are connected to the base, and/or the driving profile comprises a base which has a greater circumference than a circumference of the shaft and/or is integrally connected to the shaft.

13. The system according to claim 11, wherein the base and the shaft are formed in one piece, and/or the at least two holding members are designed as lugs and have a substantially round or polygonal circumference.

14. The system according to claim 11, wherein the at least two holding members have a substantially round circumference and/or each have a circumferential groove, and/or the base comprises at least one positioning member.

15. The implant according to claim 11, wherein at least one fixing member is arranged on both the underside of both the clamping surface and an underside of the at least one projection.

* * * * *